(12) United States Patent
Prozzo

(10) Patent No.: US 11,644,450 B2
(45) Date of Patent: May 9, 2023

(54) DIFFERENTIAL MONITORING SYSTEMS FOR CARBON DIOXIDE LEVELS AS WELL AS METHODS OF MONITORING SAME

(71) Applicant: BACHARACH, INC., New Kensington, PA (US)

(72) Inventor: Christopher D. Prozzo, Saxtons River, VT (US)

(73) Assignee: BACHARACH, INC., New Kensington, PA (US)

( * ) Notice: Subject to any disclaimer, the term of this patent is extended or adjusted under 35 U.S.C. 154(b) by 381 days.

(21) Appl. No.: 16/852,466

(22) Filed: Apr. 18, 2020

(65) Prior Publication Data

US 2020/0340964 A1 Oct. 29, 2020

Related U.S. Application Data

(60) Provisional application No. 62/836,657, filed on Apr. 20, 2019.

(51) Int. Cl.
*G01N 33/00* (2006.01)
*G01F 3/22* (2006.01)
*G01F 7/00* (2006.01)

(52) U.S. Cl.
CPC ........... *G01N 33/004* (2013.01); *G01F 3/224* (2013.01); *G01F 7/005* (2013.01)

(58) Field of Classification Search
CPC .................................................. G01N 33/004
See application file for complete search history.

(56) References Cited

U.S. PATENT DOCUMENTS 5,394,934 A 3/1995 Rein et al.
6,222,456 B1 4/2001 Tice
(Continued)

FOREIGN PATENT DOCUMENTS

| EP | 3 418 644 A1 | 12/2018 |
| WO | WO 95/06926 | 3/1995 |
| WO | WO 2014/120801 A1 | 8/2014 |

OTHER PUBLICATIONS

International Search Report dated Sep. 28, 2020 corresponding to International Application No. PCT/US2020/028893.

(Continued)

*Primary Examiner* — Paul M. West
(74) *Attorney, Agent, or Firm* — Bartony & Associates LLC

(57) ABSTRACT

A differential monitoring system of carbon dioxide levels within an associated building with a monitoring zone including a quantity of captured carbon dioxide and a reference zone that is spaced away from the monitoring zone. The differential monitoring system includes a first carbon dioxide monitoring inlet disposed within the monitoring zone. A second carbon dioxide monitoring inlet is disposed within the monitoring zone in spaced relation to the first carbon dioxide monitoring inlet and/or is disposed within the reference zone in spaced relation to the first carbon dioxide monitoring zone. A controller is operable to determine when a carbon dioxide level at the second carbon dioxide monitoring inlet exceeds a carbon dioxide level at the first carbon dioxide monitoring inlet by a predetermined differential threshold. The inlets can be part of an aspirated sampling system and/or part of a distributed sensor system. Methods of monitoring carbon dioxide levels are also included.

20 Claims, 9 Drawing Sheets

(56) References Cited

U.S. PATENT DOCUMENTS

| | | |
|---|---|---|
| 6,467,696 B2 | 10/2002 | Riley et al. |
| 7,333,129 B2 | 2/2008 | Miller et al. |
| 8,147,302 B2 | 4/2012 | Desrochers et al. |
| 8,491,710 B2 | 7/2013 | Meirav |
| 9,470,670 B2 | 10/2016 | Angeli et al. |
| 10,086,324 B2 | 10/2018 | Meirav |
| 10,145,831 B2 | 12/2018 | Angeli et al. |
| 10,192,411 B2 | 1/2019 | Wedig et al. |
| 10,232,684 B2 | 3/2019 | Tajima et al. |
| 2002/0157447 A1 | 10/2002 | Schell |
| 2006/0234621 A1 | 10/2006 | Desrochers et al. |
| 2013/0181617 A1 | 7/2013 | Maddox |
| 2013/0282183 A1 | 10/2013 | Miller et al. |
| 2017/0241964 A1 | 8/2017 | Vereecken et al. |
| 2018/0187937 A1 | 7/2018 | Kujak |
| 2018/0299153 A1 | 10/2018 | Ajax et al. |
| 2018/0363939 A1 | 12/2018 | McCormick et al. |
| 2019/0285747 A1 | 9/2019 | Yakymyshyn |
| 2020/0278741 A1* | 9/2020 | Madhusudhana ..... G06F 1/1694 |

OTHER PUBLICATIONS

Written Opinion dated Sep. 28, 2020 corresponding to International Application No. PCT/US2020/028893.
International Preliminary Report on Patentability (IPRP) dated Sep. 28, 2021 in International Application No. PCT/US2020/028893 (7 pages).
Ayers, Jason, article titled "Is CO2 The Natural Choice for Food Retailers?", the News, Nov. 5, 2019.
Ayers, Jason, article titled "is CO2 the Natural Refrigerant Choice?", https://blog.mybacharach.com/articles/co2-natural-refrigerant-choice/, Oct. 8, 2019.

* cited by examiner

DIFFERENTIAL MONITORING SYSTEMS FOR CARBON DIOXIDE LEVELS AS WELL AS METHODS OF MONITORING SAME

This application claims priority from and benefit of the filing date of U.S. Provisional Patent Application No. 62/836,657, filed on Apr. 20, 2019, the content of which is hereby expressly incorporated herein by reference in its entirety.

BACKGROUND

The subject matter of the present disclosure broadly relates to the art of refrigeration systems and, more particularly, to systems and methods operable to identify potential refrigerant-loss events in carbon dioxide-based refrigeration systems that are used in connection with environments that experience time-variable, respirated-carbon dioxide levels, such as may be associated with transient human occupancy, for example.

It will be appreciated that the subject matter of the present disclosure may find particular application and use in conjunction with enclosed spaces, such as retail warehouse store facilities, for example, that contain coolers, freezers and/or other cold-storage units, and will be illustrated and described herein with particular reference thereto. However, it is to be recognized and understood that the subject matter of the present disclosure is amenable to use in other applications and/or environments, such as medical, commercial and/or industrial spaces having cold-storage or other climate-controlled areas and/or appliances, for example, and that the configurations shown and described herein are merely exemplary and not intended to be limiting.

Refrigeration systems of various types, kinds and constructions are known and commonly used in connection with the manufacture and operation of coolers, refrigerators, freezers and/or other cold-storage equipment installed within buildings and other enclosed spaces. In some cases, known refrigeration systems can use the flow of pressurized refrigerant through a conventional refrigeration cycle to transfer heat out of the climate-controlled appliance or area. Though many known refrigerant substances exhibit acceptable performance levels during use, it has been recognized that some refrigerants present environmental and/or human health hazards when inadvertently vented from the refrigeration system into the external atmosphere. Non-limiting examples of such refrigerants include chlorofluorocarbons (CFCs), hydrochlorofluorocarbons (HCFCs) and hydrofluorocarbons (HFCs).

In an effort to mitigate undesirable environmental impacts and hazardous effects of known refrigerant compounds, refrigeration systems that use other substances as the heat transfer medium have been developed. As one example, refrigeration systems that utilize pressurized carbon dioxide as the refrigeration medium continue to gain acceptance and grow in use in retail, commercial and other settings due at least in part to the low global warming potential (GWP) value of carbon dioxide relative to the conventional refrigerant substances discussed above. So, while refrigeration systems that utilize pressurized carbon dioxide will still experience inadvertent pressurized gas loss, it is expected that the undesirable environmental impacts and hazardous effects of such events will be greatly reduced in comparison with the release of other known refrigerant substances.

The inadvertent loss of refrigerant medium into an ambient atmosphere can significantly reduce performance of the associated refrigeration system. Additionally, substantial cost is often associated with repair and subsequent recharging of refrigeration systems with the requisite amount of refrigerant. For these and other reasons, facilities that include coolers, refrigeration units, freezers and/or other cold-storage spaces commonly install a refrigerant monitoring and/or leak detection system to aid in quickly identifying refrigerant-loss events. In cases in which the refrigerant being monitored is normally substantially-absent from the ambient atmosphere, such monitoring and/or leak detection systems issue notifications when the refrigerant is detected in the ambient atmosphere even at very low levels (e.g., less than 10 ppm).

However, in addition to being a natural constituent of ambient atmosphere, levels of carbon dioxide within an enclosed space can vary significantly over time which makes it difficult to detect a leak from a refrigeration system using absolute concentration data. For example, respirated carbon dioxide levels vary widely as human activity within the enclosed space changes, such as the carbon dioxide levels in a retail warehouse store when the store is closed compared with peak activity on a weekend or holiday. Unfortunately, conventional monitoring and/or leak detection systems, such as those that detect minute amounts of a refrigerant compound or that compare detected levels of a refrigerant compound with fixed threshold value, are often inadequate when used in connection with monitoring and/or leak detection of facilities that include climate-controlled appliances and/or areas that utilize carbon dioxide as a refrigerant, particularly when ambient levels of carbon dioxide fluctuate over time under normal conditions.

As such, it is believed desirable to develop systems and methods of identifying potential refrigerant-loss events associated with carbon dioxide-based refrigeration units that aid in addressing the foregoing and/or other deficiencies associated with conventional refrigerant monitoring and/or leak detection systems, and/or otherwise advance the art of refrigeration systems.

SUMMARY

In accordance with one aspect of the present disclosure, a differential monitoring system is configured to monitor carbon dioxide levels of an associated atmosphere within an associated building that has an associated monitoring zone. The differential monitoring system can include a first monitoring inlet disposed within the associated monitoring zone. The differential monitoring system can further include a monitoring unit including a controller operable to compare a carbon dioxide level at said first monitoring inlet with a reference carbon dioxide level and determine when said carbon dioxide level at said first monitoring inlet exceeds said reference carbon dioxide level by at least a predetermined differential threshold.

In accordance with a further aspect of the present disclosure, a differential monitoring method is provided for monitoring carbon dioxide levels within an associated building comprising a monitoring zone including an associated quantity of captured carbon dioxide. The method can include determining a first carbon dioxide concentration level in the monitoring zone and determining a reference carbon dioxide concentration level. The method can further include determining if the first carbon dioxide concentration level exceeds the reference carbon dioxide concentration level by at least a differential threshold. An alert may be initiated if the first carbon dioxide concentration level exceeds the reference carbon dioxide concentration level by at least a differential threshold.

One example of a monitoring system in accordance with the subject matter of the present disclosure can be operable to monitor carbon dioxide levels within an associated building that has (i) an associated monitoring zone including an associated quantity of captured carbon dioxide, and/or (ii) an associated atmospheric reference zone that is spaced away from the associated monitoring zone. The monitoring system can include a first carbon dioxide monitoring inlet disposed within the associated monitoring zone. A second carbon dioxide monitoring inlet is disposed within the associated monitoring zone in spaced relation to the first carbon dioxide monitoring inlet and/or disposed within the associated atmospheric reference zone in spaced relation to the first carbon dioxide monitoring zone. A controller is operable to determine when a carbon dioxide level at the first carbon dioxide monitoring inlet exceeds a carbon dioxide level at the second carbon dioxide monitoring inlet by a predetermined differential threshold.

One example of a method in accordance with the subject matter of the present disclosure can be operable to monitor carbon dioxide levels within an associated building that has (i) an associated monitoring zone including an associated quantity of captured carbon dioxide, and/or (ii) an associated atmospheric reference zone that is spaced away from the associated monitoring zone. The method can include determining a first carbon dioxide level within the associated monitoring zone. The method can also include determining one or more additional carbon dioxide levels within the associated monitoring zone and/or the associated atmospheric reference zone. The method can further include determining when the first carbon dioxide level exceeds the one or more additional carbon dioxide levels by a predetermined differential threshold.

DETAILED DESCRIPTION

Figure 1:
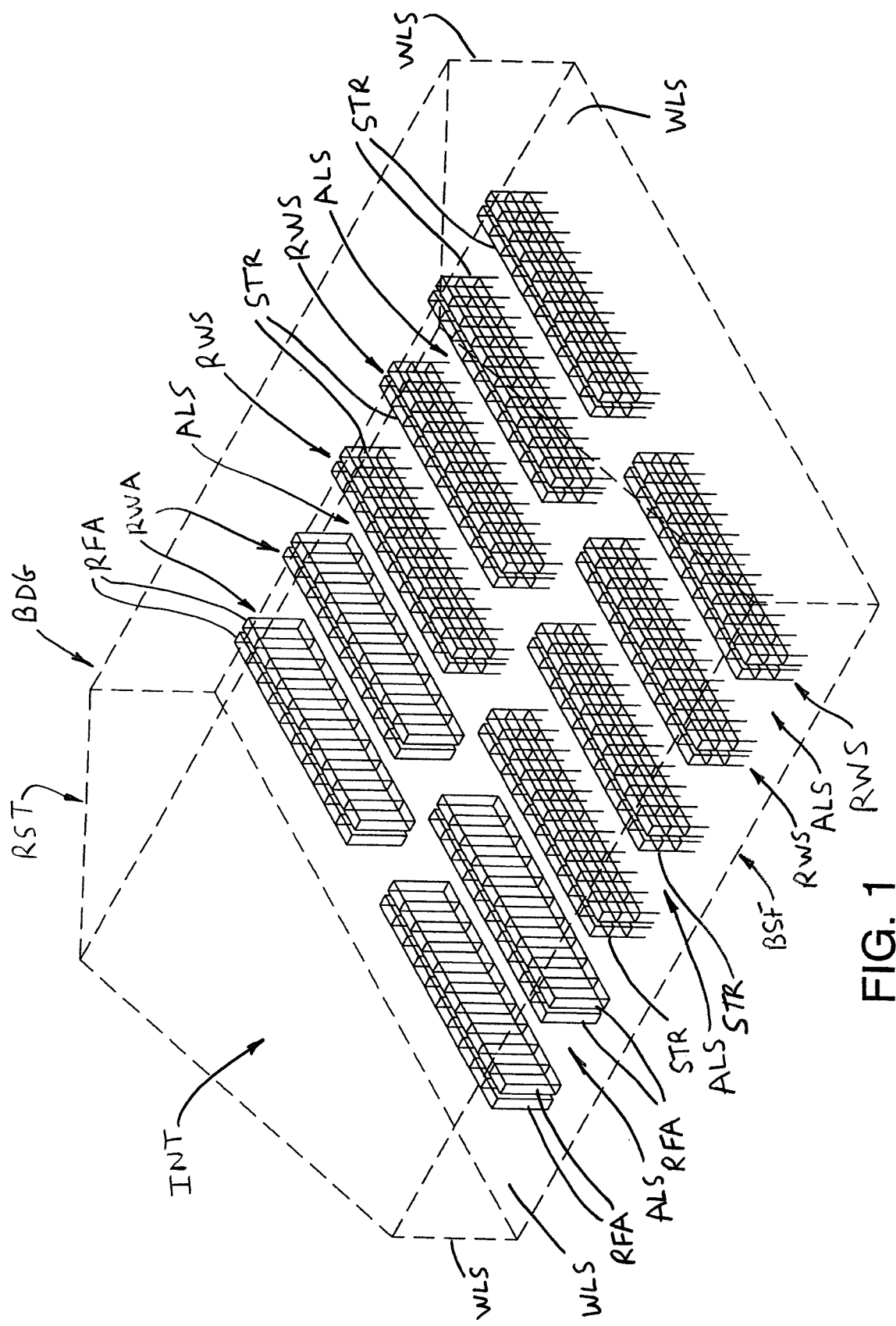
FIG. 1 is schematic representation of a facility including carbon dioxide-based refrigeration units and a monitoring system in accordance with the subject matter of the present disclosure.

As used herein, terms such as "data", "values", "information", "signals" and the like are used interchangeably herein to broadly refer to analog and/or digital communications, such as may be transferred, stored, retrieved and/or otherwise exchanged between components and/or systems in any suitable manner.

Turning now to the drawings, it is to be understood that the showings are for purposes of illustrating examples of the subject matter of the present disclosure and are not intended to be limiting. Additionally, it will be appreciated that the drawings are not to scale and that portions of certain features and/or elements may be exaggerated for purpose of clarity and ease of understanding.

FIGS. 1-4 illustrate an example of a building BDG that includes one or more areas or zones containing or otherwise operatively associated with coolers, refrigerators, freezers and/or other cold-storage equipment, such as may be used for short-term and/or long-term storage of foodstuffs and/or other goods under climate-controlled conditions. Non-limiting examples of such buildings can include commercial and/or industrial cold-storage facilities, medical facilities, distribution centers, and retail and/or wholesale sales facilities, such as warehouse stores, for example. As such, it will be appreciated that the subject matter of the present disclosure is not intended to be limited to installation and/or use in association with buildings of any particular type, kind, size and/or construction.

Building BDG is shown as including a base surface BSF on or along which cold-storage equipment and other storage racks can be positioned. It will be appreciated that base surface BSF can be of any suitable type, kind and/or construction, such as an interior floor, for example. Building BDG includes a roof structure RST that extends across at least a portion of base surface BSF. A plurality of walls WLS extend between base surface BSF and roof structure RST, and at least partially enclose the building to form an interior space INT thereof.

Interior space INT of building BDG can include any suitable number of one or more areas or zones containing or otherwise operatively associated with one or more coolers, refrigerators, freezers and/or other cold-storage equipment, such as may be used for short-term and/or long-term storage of foodstuffs and/or other goods under climate-controlled conditions. Additionally, it will be appreciated that such coolers, refrigerators, freezers and/or other cold-storage equipment can be positioned, organized or otherwise arranged in any suitable manner relative to one another and/or any associated storage facility features (e.g., walls). In the arrangement shown in FIGS. 1-4, for example, interior space INT includes a plurality of conventional storage racks STR arranged in a plurality of rows RWS and a plurality refrigeration appliances RFA arranged in a plurality of rows RWA. Two or more of rows RWS and/or RWA can be spaced apart from one another such that one or more aisles ALS are formed along one of the rows and/or between adjacent ones of a plurality of rows. Though storage racks STR and refrigeration appliances RFA are shown as being arranged in different areas of interior space INT, it is to be appreciated and understood that the subject matter of the present disclosure can be used in connection with any other configuration and/or arrangement of refrigerated and non-refrigerated appliances and/or other equipment.

Figure 2:
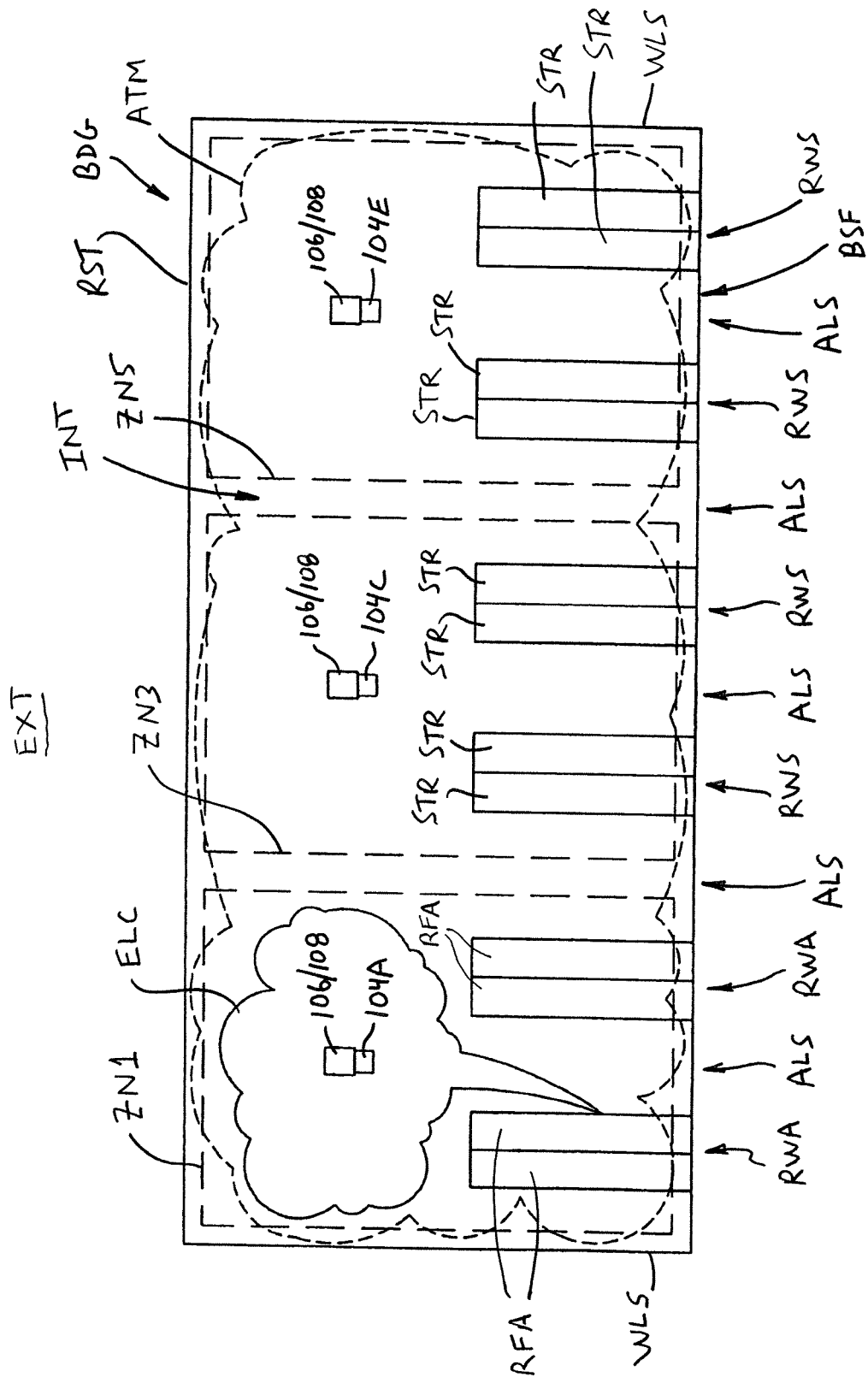
FIG. 2 is a side elevation view of the exemplary facility in FIG. 1 illustrating a monitoring system in accordance with the subject matter of the present disclosure operatively associated with exemplary monitoring and atmospheric reference zones.
Figure 3:
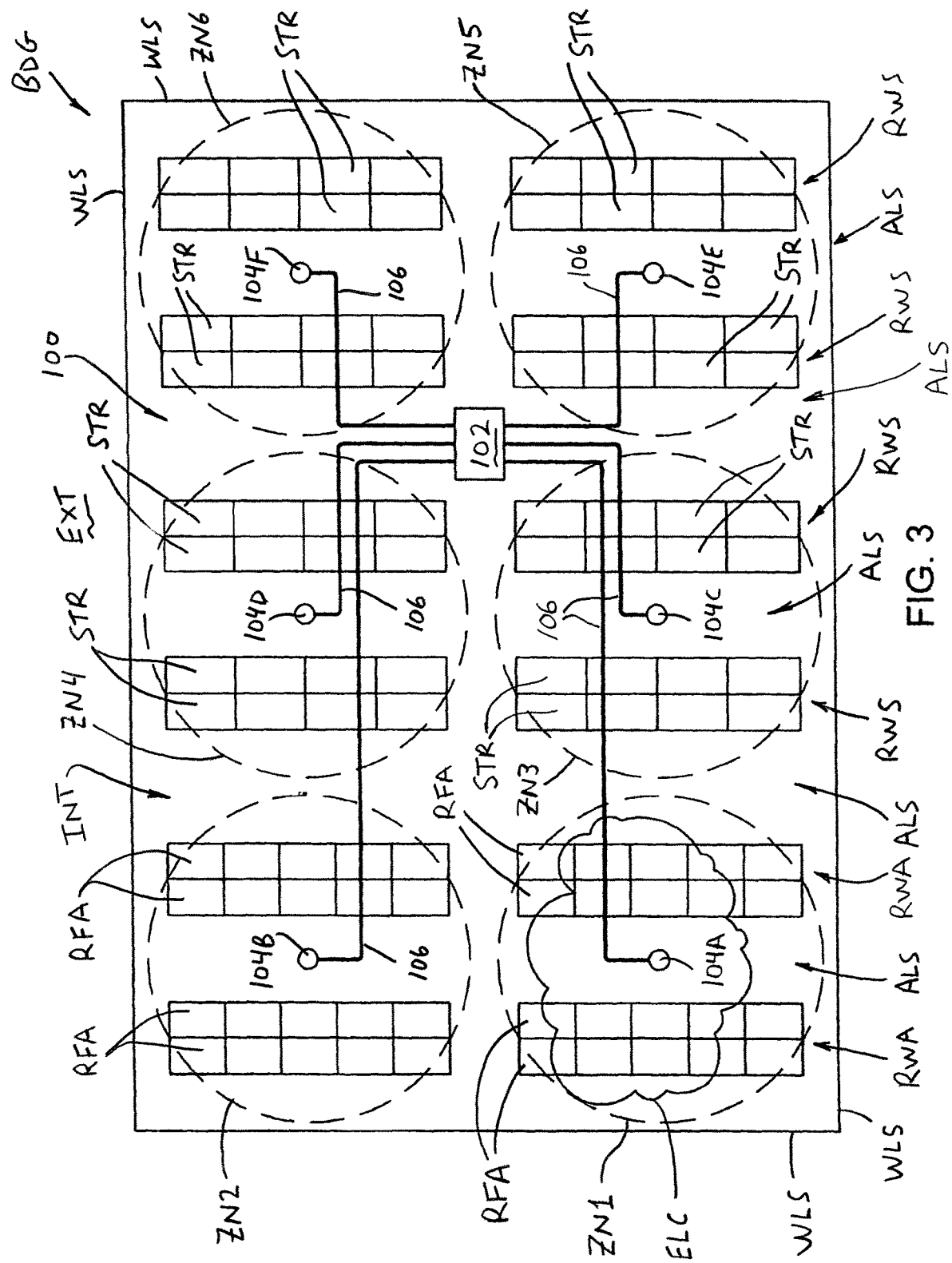
FIG. 3 is a top plan view of the exemplary facility in FIGS. 1 and 2 illustrating a monitoring system in accordance with the subject matter of the present disclosure including aspirated monitoring inlets.
Figure 4:
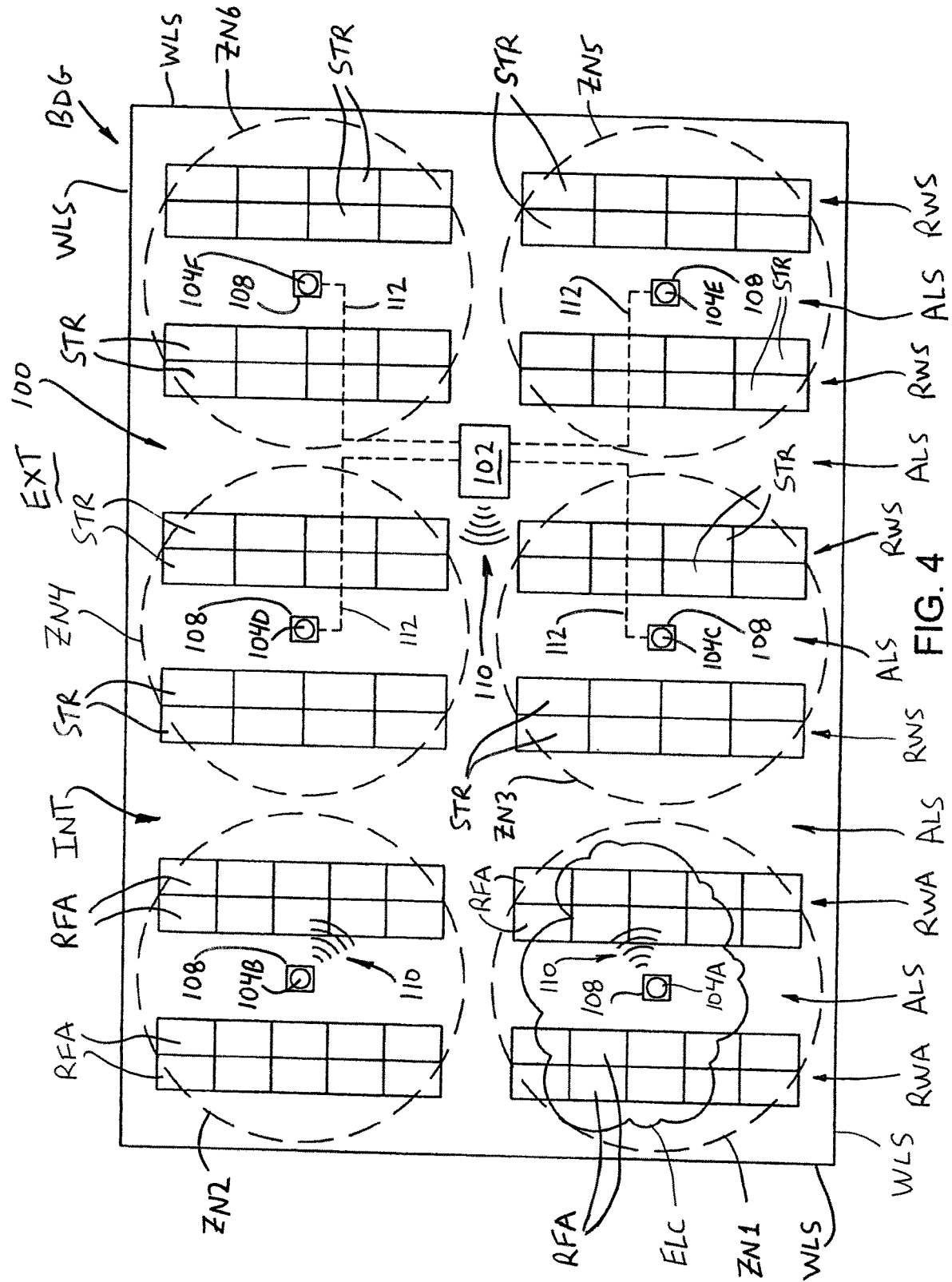
FIG. 4 is a top plan view of the exemplary facility in FIGS. 1 and 2 illustrating a monitoring system in accordance with the subject matter of the present disclosure including sensors with monitoring inlets.

As identified in FIGS. 2-4, interior space INT can include one or more areas or zones within which storage racks STR are installed and/or one or more areas or zones within which refrigeration appliances RFA are installed. As a non-limiting example, interior space INT is shown as including areas or zones ZN1 and ZN2 within which refrigeration appliances RFA are located as well as areas or zones ZN3, ZN4, ZN5 and ZN6 within which storage racks STR are located. It will be appreciated that an internal atmosphere ATM (FIG. 2) will exist within interior space INT and that an external atmosphere EXT will exist outside of the interior space and/or building BDG. Zones ZN1-ZN6 are shown as containing portions of internal atmosphere ATM. It will be appreciated that the movement and dispersion of constituent gases within internal atmosphere ATM flowing within, through and/or otherwise between different ones of zones ZN1-ZN6 will be substantially influenced by mechanical, structural and/or other features of building BDG in and around interior space INT. As such, it is to be recognized and understood that the demarcations represented by zones ZN1-ZN6 are merely for discussion purposes and not intended to be in any way limiting.

In accordance with the subject matter of the present disclosure, a monitoring system 100 is installed in operative association with interior space INT, such as by mounting one or more components thereof on or along structures (e.g., walls, ceilings, floors, etc.) of building BDG. Monitoring system 100 can include a monitoring unit 102 and two or more monitoring inlets in fluid communication with an atmosphere to be monitored. It will be appreciated that the monitoring system 100 can include any suitable quantity of two or more monitoring inlets operatively associated therewith, such as from two (2) to two hundred (200) monitoring inlets, for example. Additionally, it will be appreciated that the two or more monitoring inlets can be spaced apart from one another within one or more areas, spaces and/or buildings in any suitable configuration and/or arrangement.

As one non-limiting example, monitoring system 100 is shown in FIGS. 2-4 as including a plurality of monitoring inlets 104A-104F disposed within internal atmosphere ATM of interior space INT. It is to be recognized and understood that, though shown in the exemplary arrangement in FIGS. 2-4 as being distributed throughout a single interior space, the two or more monitoring inlets can be placed in any number of one or more spaces, areas, buildings and/or locations. That is, it is to be recognized and understood that a given monitoring system can be operatively associated with any number of one or more interior atmospheres, such as by receiving and/or analyzing gas samples, information, data and/or signals from monitoring inlets in fluid communication with a single interior atmosphere or two or more interior atmospheres such as may be spaced apart or otherwise at least partially isolated from one another (e.g., separate stores in a shopping mall, separate buildings of a cold-storage facility), and that all such configurations and arrangements are intended to find full support in the subject application.

In the exemplary arrangement shown in FIGS. 2-4, monitoring inlet 104A is operatively disposed within monitoring zone ZN1 and monitoring inlet 104B is operatively disposed within monitoring zone ZN2 with monitoring inlets 104C-104F operatively disposed within monitoring zones ZN3-ZN6, respectively. As such, the monitoring inlets are spaced apart from one another and in spaced relation to monitoring unit 102. It will be appreciated that the two or more monitoring inlets can be operatively associated with the corresponding monitoring unit in any suitable manner. As one example, one or more of monitoring inlets 104A-104F can be fluidically coupled with monitoring unit 102 by way of gas transfer lines 106, such as is shown in FIG. 3, for example. In such an arrangement, monitoring unit 102 can be operable to selectively draw gas samples from interior atmosphere INT through individual ones of monitoring inlets 104A-104F. As a non-limiting example, monitoring unit 102 can sequentially draw gas samples from zone ZN1, zone ZN2 and/or, optionally, one or more of zones ZN3-ZN6 of interior atmosphere INT through a respective one of monitoring inlets 104A-104F such that individual gas samples from zone ZN1, zone ZN2 and/or, optionally, one or more of zones ZN3-ZN6 can be separately monitored by monitoring unit 102.

Additionally, or in the alternative, a monitoring system 100 in accordance with the subject matter of the present disclosure can include one or more monitoring inlets that are communicatively coupled with the monitoring unit 102, such as by way of one or more wired connections, one or more wireless connections and/or one or more connections to a distributed computer network, such as the Internet. In such cases, monitoring system 100 can include sensors 108 operatively associated with monitoring inlets 104A-104F. In such an arrangement, gas samples at each monitoring inlet can be sensed or otherwise analyzed locally by the associated sensor 108 with data, information and/or signals communicated from sensors 108 to monitoring unit 102 in a suitable manner.

In the exemplary arrangement shown in FIG. 4, sensors 108 of one or more of the monitoring inlets (e.g., monitoring inlets 104A and 104B) can be communicatively coupled with monitoring unit 102 by way of wireless connections, which are represented by waves 110. Additionally, or in the alternative, sensors 108 of one or more of the monitoring inlets (e.g., monitoring inlets 104C-104F) can be communicatively coupled with monitoring unit 102 by wired connections, which are represented by dashed lines 112. It will be appreciated that the wireless and/or wired connections can include direct communications between the sensors and the monitoring unit and/or can include indirect communications between the sensors and the monitoring unit, such communicative coupling by way of a distributed computer network 114 (e.g., the Internet).

In accordance with the subject matter of the present disclosure, monitoring system 100 is operatively associated with environments in which one or more quantities of pressurized carbon dioxide ($CO_2$) refrigerant are captured within or otherwise operatively associated with one or more refrigeration appliances RFA or other climate control units, such as have been discussed above. A building zone that includes one or more quantities of pressurized carbon dioxide refrigerant captured within or otherwise operatively associated with a source such as one or more refrigeration appliances RFA or other climate control units, such as first and second zones ZN1,ZN2 in the present example, can be referred to as a "potential leak zone." For purposes of discussion, FIGS. 2-4 illustrate an elevated concentration ELC of carbon dioxide within zone ZN1, such as may be associated with an event in which carbon dioxide refrigerant inadvertently escapes from one or more of refrigeration appliances RFA within zone ZN1. It will be appreciated that size, shape and position of the demarcation of elevated concentration ELC is merely exemplary, and that elevated concentration levels of carbon dioxide from a leak event may be present at any number of one or more monitoring inlets.

Figure 5:
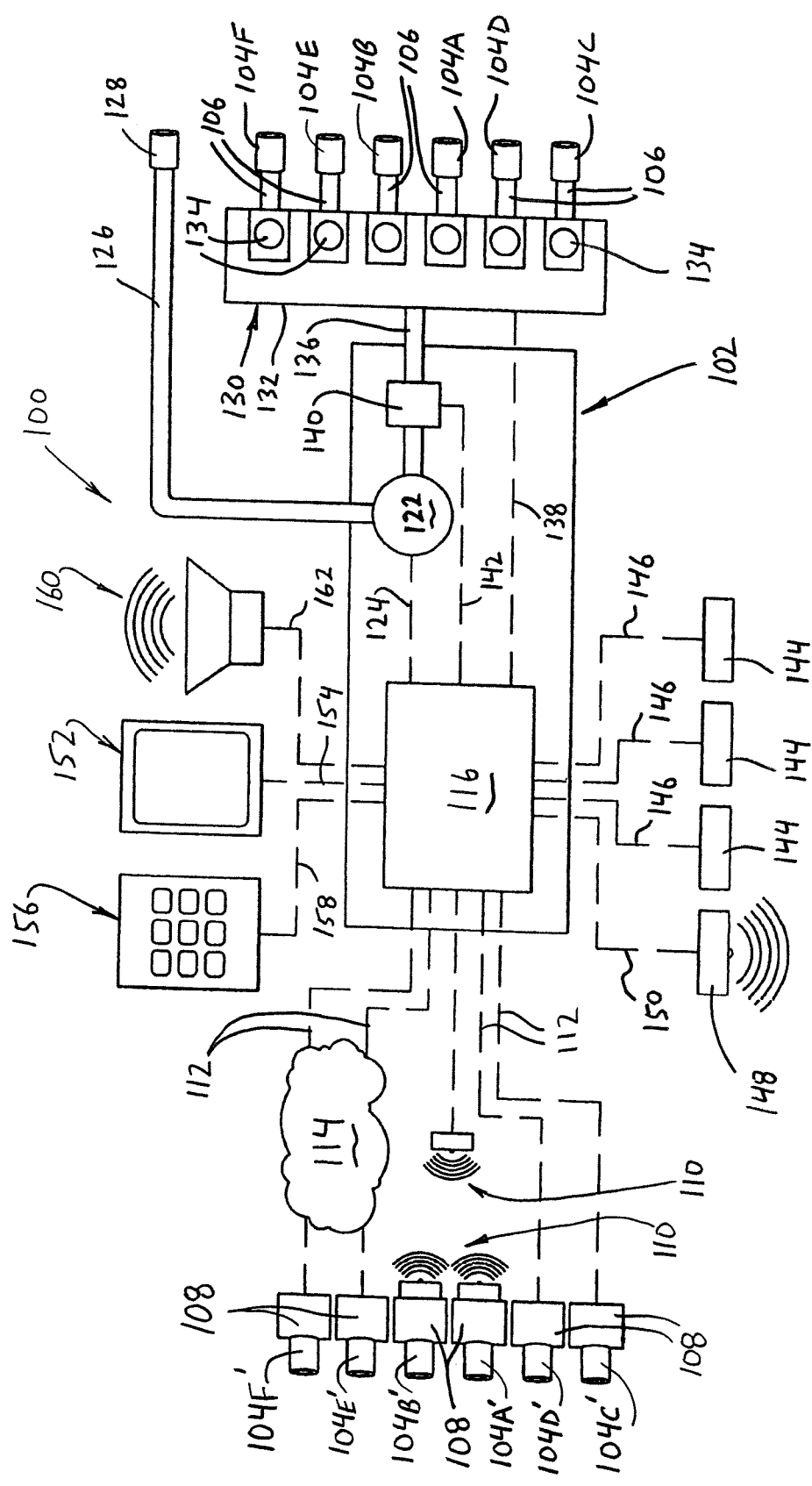
FIG. 5 is a schematic representation of one example of a monitoring system in accordance with the subject matter of the present disclosure.

FIG. 5 is a schematic representation of one example of monitoring system 100. In addition to sampling carbon dioxide levels (i.e., concentrations in terms of %, parts per million, or other concentration data) within one or more areas, zones and/or internal atmospheres, monitoring system 100 is operable to identify or otherwise determine when leak events may be occurring or may have occurred by comparing the carbon dioxide level at one monitoring inlet with current carbon dioxide levels at one or more other monitoring inlets, such as by way of one or more of the methods, processes and/or logic operations discussed hereinafter. As such, monitoring unit 102 can include any suitable hardware, software and/or combination thereof for sending, receiving and/or otherwise communicating signals, data, values, instructions and/or information to, from and/or otherwise between the monitoring unit and any one or more of the devices and/or components of monitoring system 100. For example, monitoring unit 102 can include a controller or electronic control unit (ECU) 116 communicatively coupled with various devices and components of system 100, as discussed hereinafter.

It will be appreciated that controller 116 can include a combination of components of any suitable type, kind and/or configuration, such as a microprocessor, for example, for processing data, executing software routines/programs, and other functions relating to the performance and/or operation of monitoring system 100. Additionally, controller 116 can include a memory of any suitable type, kind and/or configuration that can be used to store software, parameters, settings, inputs, data, values and/or other information for use in association with the performance and/operation of monitoring system 100. In the arrangement shown in FIG. 6, controller 116 includes a processing device 118 and a memory 120, which is represented by boxes 120A and 120B.

As discussed above, monitoring system 100 can include two or more monitoring inlets 104A-104F operatively associated therewith. In some cases, one or more of the monitoring inlets can be connected in fluid communication with the monitoring unit 102 such that gas samples can be drawn from the associated atmosphere and into the monitoring unit 102 for analysis. Additionally, or in the alternative, one or more of the monitoring inlets 104A-104F can be operatively associated with a sensor 108 that is separate from the monitoring unit 102. In such cases, gas samples can be drawn from the associated atmosphere and analyzed by the associated sensor 108. Data, information and/or signals generated by the sensor 108 having a relation to the analysis of the gas samples can be communicated to the monitoring unit 102 in a suitable manner, as discussed above. Monitoring system 100 is shown in FIG. 5 as including monitoring inlets that correspond to the aspirated system shown and described in connection with FIG. 3 as well as monitoring inlets that correspond to monitoring inlets of the discrete sensor system shown and described in connection with FIG. 4. For purposes of clarity of discussion only and without limiting the subject application, monitoring inlets 104A-104F of FIG. 4 are identified in FIG. 5 with an apostrophe (i.e., as monitoring inlets 104A'-104F'). Thus, those of ordinary skill in the art will recognize that the terms "inlet" or "monitoring inlet" can relate to a carbon dioxide inlet 104A-104F of an aspirated system 100 such as shown in FIG. 3 or can relate to a carbon dioxide inlet 104A'-104F' or sensing chamber or sensing region of a carbon dioxide sensor 108 that is remotely located from the monitoring unit 102 and connected to the monitoring unit 102 by a suitable wired or wireless network connection as shown for the system 100 of FIG. 4.

It is to be recognized and understood that any combination of aspirated monitoring inlets and monitoring inlets of discrete sensors can be used and that all such constructions are intended to find full support in the subject application. That is, a monitoring system 100 in accordance with the subject matter of the present disclosure can include only a plurality of aspirated monitoring inlets 104A-104F (e.g., FIG. 3). Alternately, a monitoring system 100 in accordance with the subject matter of the present disclosure can include only a plurality of monitoring inlets 104A'-104F' associated with discrete sensors (e.g., FIG. 4). As a further alternative, a monitoring system 100 in accordance with the subject matter of the present disclosure can include one or more aspirated monitoring inlets 104A-104F and one or more monitoring inlets of discrete sensors 104A'-104F'.

In cases in which one or more aspirated monitoring inlets 104A-104F are included, monitoring system 100 can include a gas displacement device, such as may be selectively operable to transfer gases into and/or out of monitoring unit 102, for example. It will be appreciated that a gas displacement device of any suitable size, type, configuration and/or construction can be used. For example, monitoring unit 102 is shown in FIG. 5 as including a pump 122 that is communicatively coupled with controller 116, such as by way of an electrical conductor or lead 124, for example. As such, pump can be selectively operated to draw gas samples into monitoring unit 102 and/or to purge or otherwise evacuate gases from the monitoring unit, such as through a gas exhaust line 126 and/or an exhaust port 128, for example.

In such cases, monitoring system 100 can also include a control device that is selectively operable to place one or more of monitoring inlets 104A-104F in fluid communication pump 122 such that gas samples can be drawn into monitoring unit 102 for analysis. In some cases, the control device can be included on or in the monitoring unit. In other cases, the control device can be provided separately from the monitoring unit. As a non-limiting example, monitoring system 100 can include a control device such as a valve assembly 130 that includes a valve body 132 with valves 134 operatively connected between one of monitoring inlets 104A-104F and an inlet passage 136. Valve assembly 130 can be communicatively coupled with controller 116, such as by way of an electrical conductor or lead 138, for example, such that controller 116 can selectively operate individual ones of valves 134 so that pump 122 can draw individual gas samples through monitoring inlets 104A-104F in a predetermined or other sequence.

Monitoring unit 102 can also include one or more sensing channels, such as may be suitable for measuring, identifying or otherwise determining one or more properties and/or characteristics of the gas samples drawn through the monitoring inlets, and communicating signals, data, values and/or information having a relation to such one or more properties and/or characteristics to controller 116. It will be appreciated that the one or more sensing channels can take any suitable form and can be of any suitable type, kind and/or arrangement. For example, a sensing channel can include one or more devices, components and/or systems for measuring, identifying or otherwise determining one or more properties and/or characteristics of the gas samples, which devices, components and/or systems will collectively be referred to herein as "sensors". Additionally, it will be appreciated that such sensors can be of any suitable type, kind, construction, configuration and/or arrangement. As non-limiting examples, one or more of the sensors can be of the type and/or kind that measure, identify or otherwise determine gas constituent and/or chemical compound concentrations. In the arrangement shown in FIG. 5, monitoring unit 102 can include a sensor 140 disposed in fluid communication between valve assembly 130 and pump 122, such as along inlet passage 136, for example. Sensor 140 can be communicatively coupled with controller 116 in a suitable manner, such as by an electrical conductor or lead 142, for example.

In cases in which one or more monitoring inlets associated with discrete sensors are included, such as is shown in FIG. 4, for example, sensors 108 are disposed in fluid communication with a corresponding one of the monitoring inlets. As shown in FIG. 5, sensors 108 that are operatively associated with monitoring inlets 104A'-104F' are communicatively coupled with controller 116 in a suitable manner, such as by way of wireless connections 110 and/or wired connections 112, for example. Additionally, as discussed above, the wireless and/or wired connections can include direct and/or indirect communications. For example, the sensors of monitoring inlets 104A'-104D' in FIG. 5 directly communicate with controller 116 whereas the sensors of monitoring inlets 104E'-104F' communicate indirectly, such as by way of distributed computer network 114 (e.g., the Internet).

It will be appreciated that sensors 108 and/or 140 can be of a type, kind and/or construction that are operative to measure or otherwise determine the presence and/or concentration of carbon dioxide within the gas samples drawn through the monitoring inlets 104A-104F (for sensor 140) or within the gas that flows into the monitoring inlets 104A'-104F' (for sensors 108). In one example, sensors 108,140 can be non-dispersive infrared (NDIR) carbon dioxide sensors or chemical gas sensors, but other carbon dioxide sensors can additionally or alternatively be used. In some cases, sensors 108 and/or 140 can have a sensitivity to measure or otherwise determine concentration levels of carbon dioxide within a predetermined range, such as from approximately zero parts per million (ppm) to approximately 40,000 ppm or more, for example, or sensors 108 and/or 140 can have a sensitivity to measure or otherwise determine concentration levels of carbon dioxide within a smaller range such as from approximately zero ppm to approximately 5,000 ppm. In some cases, monitoring unit 102 can also include one or more additional sensing channels. For example, sensors 144 are shown as being communicatively coupled with controller 116, such as by way of electrical conductors or leads 146, for example, and can be of the type and kind that are operative to measure or otherwise determine temperature, pressure and/or humidity, such as the temperature, pressure and/or humidity level of the ambient atmosphere ATM around the monitoring unit 102 or elsewhere inside the building BDG or in the external atmosphere EXT outside the building BDG, for example. Sensors 144 may also include occupancy sensors to detect human occupants of the building BDG, sensors or systems that detect sales or other movement of products being sold inside the building BDG, or sensors that detect the operative state of the HVAC system of the building BDG, for example. It will be appreciated, however, that sensors of any other suitable type, kind, configuration and/or construction could alternately be used.

The one or more sensors of a monitoring system in accordance with the subject matter of the present disclosure, such as sensors 108, 140 and/or 144 of monitoring system 100, for example, can be operative to output or otherwise generate signals, data, values and/or information corresponding or otherwise having a relation to the one or more properties and/or characteristics of the gases and/or conditions that are being measured, identified or otherwise determined by a given sensor. It will be appreciated that such signals, data, values and/or information can be transmitted or otherwise communicated to, from and/or between a sensor and the controller in any suitable manner, such as by way of analog signals and/or digital communications, for example. As one non-limiting example, one or more of sensors 108 and 140 could transmit or otherwise communicate analog signals and/or digital messages to controller 116 corresponding to the presence and/or concentration of carbon dioxide within the gas samples.

A monitoring system in accordance with the subject matter of the present disclosure (e.g., system 100) can also include one or more communication channels, such as may be suitable for sending, receiving or otherwise communicating signals, data, values and/or information with one or more external devices, components and/or systems with which the monitoring system may be associated. It will be appreciated that the one or more communication channels can take any suitable form and can be of any suitable type, kind, configuration and/or arrangement. For example, each communication channel can include one or more connectors or interfaces for communicating with an associated or otherwise external device, component and/or system.

As shown in FIG. 5, for example, monitoring system 100 can, optionally, include a communication interface 148 that is communicatively coupled with controller 116 in a suitable manner, such as by way of an electrical conductor or lead 150, for example. In some cases, interface 148 can take the form of a wireless communication interface, such as, for example, may be suitable for transmitting and/or receiving data and/or information from a remote device (e.g., a phone, a personal computer, a computer network server and/or a printer). Additionally, monitoring system 100 can, optionally, include a visual communication device 152 that is communicatively coupled with controller 116 in a suitable manner, such as by way of an electrical conductor or lead 154. In some cases, visual communication device 152 can take the form of a graphical output device, such as a conventional display screen, or a graphical input/output device, such as a capacitive or resistive touch screen, for example. Monitoring system 100 can also, optionally, include a tactile input device 156, such as a keyboard or a keypad, for example, that is communicatively coupled with controller 116 in a suitable manner, such as by way of an electrical conductor or lead 158. Monitoring system 100 can, optionally, include an audible output device 160, such as a speaker, for example, that is communicatively coupled with controller 116 in a suitable manner, such as by way of an electrical conductor or lead 162.

Figure 6:
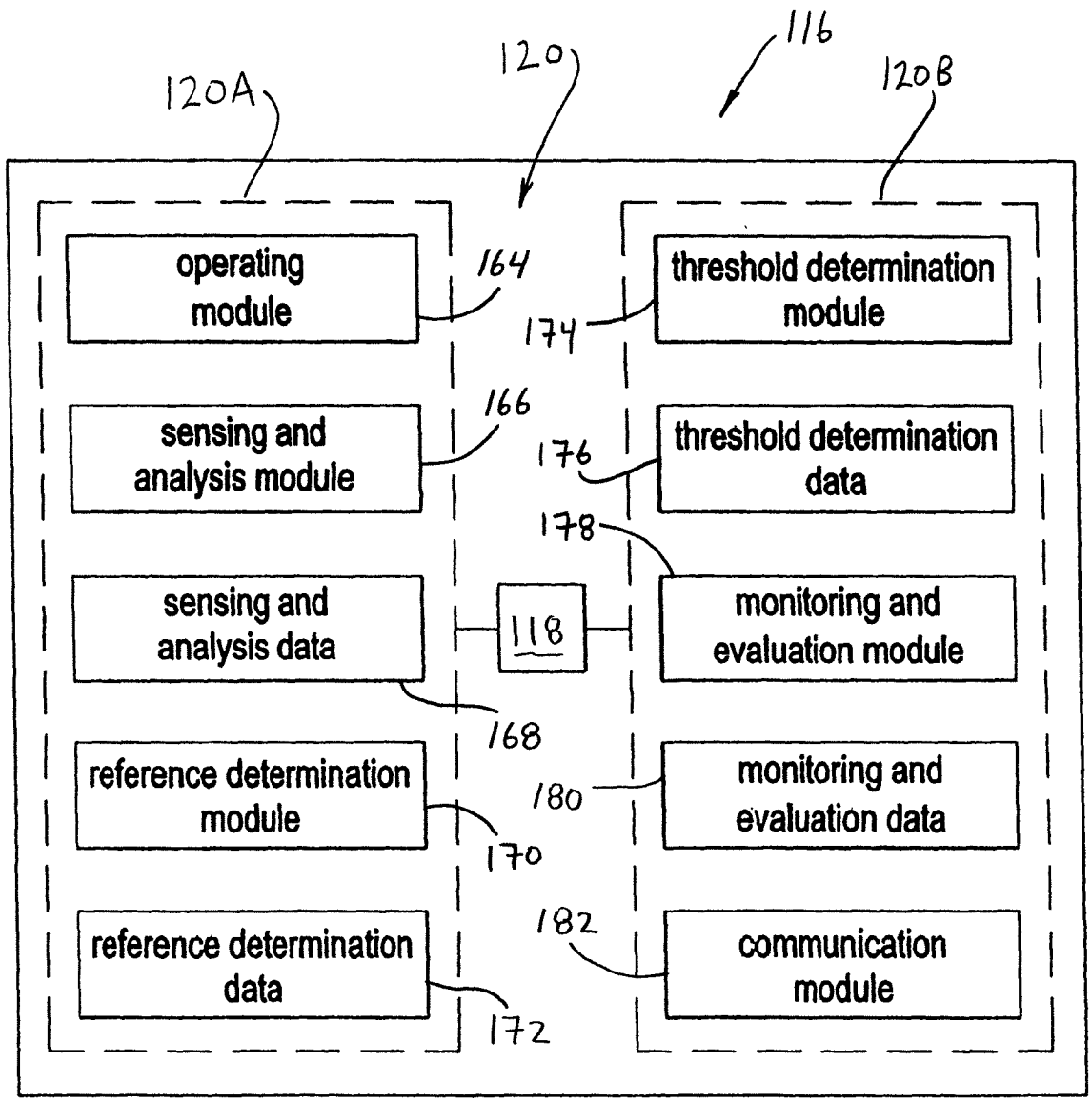
FIG. 6 is a schematic representation of one example of a controller for a monitoring system in accordance with the subject matter of the present disclosure.

With reference, now, to FIG. 6, controller 116 is discussed above as including processing device 118 that is communicatively coupled with memory 120A and 120B. Controller 116 can, optionally, include an operating module 164 that is capable of receiving, processing, storing and/or otherwise transferring data, values, information, signals and/or communications into and/or out of system 100 relating to or otherwise associated with the sampling of gases, such as through monitoring inlets 104A-104F, for example. In some cases, operating module 164 can selectively operate and/or otherwise communicate with one or more devices and/or components of system 100, such as one or more of pumps 122 and/or valve assembly 130, if included. Controller 116 can also, optionally, include a sensing and analysis module 166 that is capable of receiving, processing, storing and/or otherwise transferring data, values, information, signals and/or communications to and/or from one of more of the sensors of monitoring system 100, such as one or more of sensors 108, 140 and/or 146, for example. Data and/or information accessed, used and/or generated by sensing and analysis module 166 can be stored in memory 120, such as is represented by box 168 in FIG. 6. In some cases, data and/or information retained in memory store 168 can relate to carbon dioxide levels from one or more sensors taken at intervals over an extended period of time, such as days, weeks, months and/or years, for example.

Controller 116 can, optionally, include a reference determination module 170 that is capable of processing and storing data, values, information, signals and/or communications that may relate to carbon dioxide levels of gas samples that may be used as reference values for differential comparison with the carbon dioxide level of a given gas sample. In some cases, reference determination module 170 can apply one or more reference determination functions and/or logic algorithms to data, values, information, signals and/or communications generated and/or stored by sensing and analysis module 166, such as may be stored in box 168, as described above. Data and/or information accessed, used and/or generated by reference determination module 170 can be stored in memory 120, such as is represented by box 172 in FIG. 6. Controller 116 can also, optionally, include a threshold determination module 174 that is capable of processing and storing data, values, information, signals and/or communications that may relate to differential threshold values between reference values determined in module 170 and the carbon dioxide level of a given gas sample. In some cases, threshold determination module 174 can apply one or more threshold determination functions and/or logic algorithms to data, values, information, signals and/or communications generated and/or stored by sensing and analysis module 166, such as may be stored in box 168, as described above. As discussed above, data and/or information retained in memory store 168 can relate to carbon dioxide levels from one or more sensors taken at intervals over an extended period of time, such as days, weeks, months and/or years, for example. Additionally, data and/or information accessed, used and/or generated by threshold determination module 174 can be stored in memory 120, such as is represented by box 176 in FIG. 6.

Controller 116 can, optionally, include a monitoring and evaluation module 178 that is capable of receiving, processing and storing data, values, information, signals and/or communications that may relate to the differential comparison of reference carbon dioxide levels, such as may be determined by module 170 and/or retained in memory store 172, with the carbon dioxide level of a given gas sample, such as may be determined by module 166 and/or retained in memory store 168, relative to a differential threshold value, such as may be determined by module 174 and/or retained in memory store 176. In some cases, monitoring and evaluation module 178 can apply one or more leak determination functions and/or logic algorithms to such data, values, information, signals and/or communications and evaluate whether conditions may exist under which carbon dioxide refrigerant may be leaking into a particular area or zone. Data and/or information accessed, used and/or generated by monitoring and evaluation module 178 can be stored in memory 120, such as is represented by box 180 in FIG. 6.

Controller 116 can, optionally, include a communication module 182 that is capable of requesting, receiving, processing, storing and/or otherwise transferring data, values, information, signals and/or communications into and/or out of system 100, such as may relate to or be otherwise associated with receiving or otherwise transferring data, values, information, signals and/or communications from a remote device, such as a phone, personal computer or a computer network server, for example, such as by way of interface 148, for example. Additionally, or in the alternative, communication module 182 can be operable to communicate to a user or operator data, values, information, signals and/or communications regarding the existence of conditions in which carbon dioxide refrigerant may be leaking into a particular area or zone, such as may have been determined by module 178 and/or retained in memory store 180.

It will be appreciated that the one or more modules of controller 116, which are shown and described herein as modules 164, 166, 170, 174, 178 and 182, can be provided in any suitable manner, such as software, hardware and/or a combination of hardware and software, for example. In some cases, modules 164, 166, 170, 174, 178 and 182 can take the form of algorithms, routines and/or programs. If provided in whole or in part as software, the configuration and operation of the modules of controller 116 can be provided and stored in any suitable manner or arrangement. For example, all of the algorithms, routines and/or programs could be integrated into a single software program in which separate sections or portions of the software code will perform the various actions and/or activities of the system. In another configuration, two or more independent modules (e.g., algorithms, routines and/or programs) could be used to perform the various actions and/or activities of the system.

Furthermore, memory 120 (as represented by boxes 120A and 120B) can store or otherwise retain any suitable data, values, settings, software, algorithms, routines, programs and/or any other information, in any suitable manner or form. And, in some cases, processing device 118 can be in communication with memory 120 (as represented by boxes 120A and 120B), and can be operative to selectively access and/or process one or more of data, values, information, algorithms, routines and/or programs, such as those retained in memory stores 164, 166, 170, 174, 178 and 182 and/or memory stores 168, 172, 176 and 180, for example, alone or in combination. For example, processing device 118 can run or otherwise process an algorithm, routine or program, such as from one or more of memory locations 164, 166, 170, 174, 178 and 182 that is operative to access, analyze or otherwise utilize data and/or information, such as may be stored in one or more of memory locations 168, 172, 176 and 180.

Figure 7:
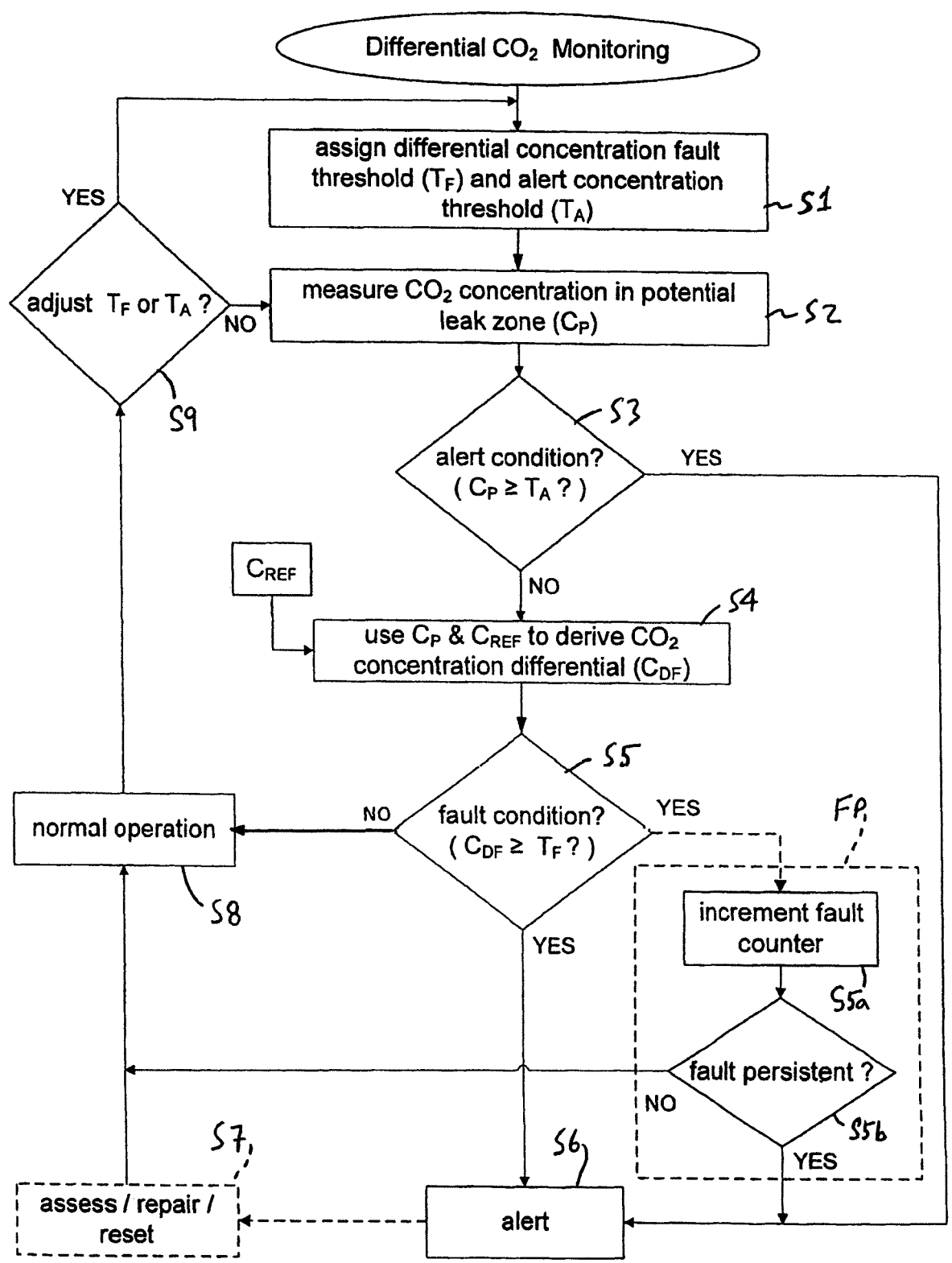
FIG. 7 is a graphical representation of one example of a method of monitoring carbon dioxide levels in accordance with the subject matter of the present disclosure.

FIG. 7 is a graphical representation of one example of a method of monitoring carbon dioxide concentration (also referred to herein as "level" or "concentration level") using a differential carbon dioxide monitoring method in accordance with the subject matter of the present disclosure. The differential carbon dioxide monitoring method can be implemented by monitoring unit 102 of system 100 to determine when a carbon dioxide leak event may be occurring or may have occurred by comparing a sensed carbon dioxide concentration $C_P$ at a monitoring inlet 104A-104F located in a potential leak zone (also referred to as a "monitoring zone") with a reference carbon dioxide concentration $C_{REF}$ of a reference zone. The reference carbon dioxide concentration can be input to or derived by monitoring unit 102 from currently sensed carbon dioxide concentrations at one or more of monitoring inlets 104A-104F located in a reference zone outside the potential leak zone such that the currently sensed carbon dioxide concentration in the potential leak zone $C_P$ is compared to a reference carbon dioxide concentration $C_{REF}$ derived from one or more current sensed carbon dioxide concentrations outside the potential leak zone. Additionally or alternatively, the reference carbon dioxide concentration $C_{REF}$ of a reference zone can be input to or derived by monitoring unit 102 from historical carbon dioxide concentrations sensed in the potential leak zone by system 100 whereby a current carbon dioxide concentration in the potential leak zone $C_P$ is compared to a reference carbon dioxide concentration $C_{REF}$ derived from a historical carbon dioxide concentration in the same zone. As such, the "reference zone" can be any one or more of zones ZN1-ZN6 that is not the potential leak zone, or the "reference zone" can be the potential leak zone, itself.

Figure 9:
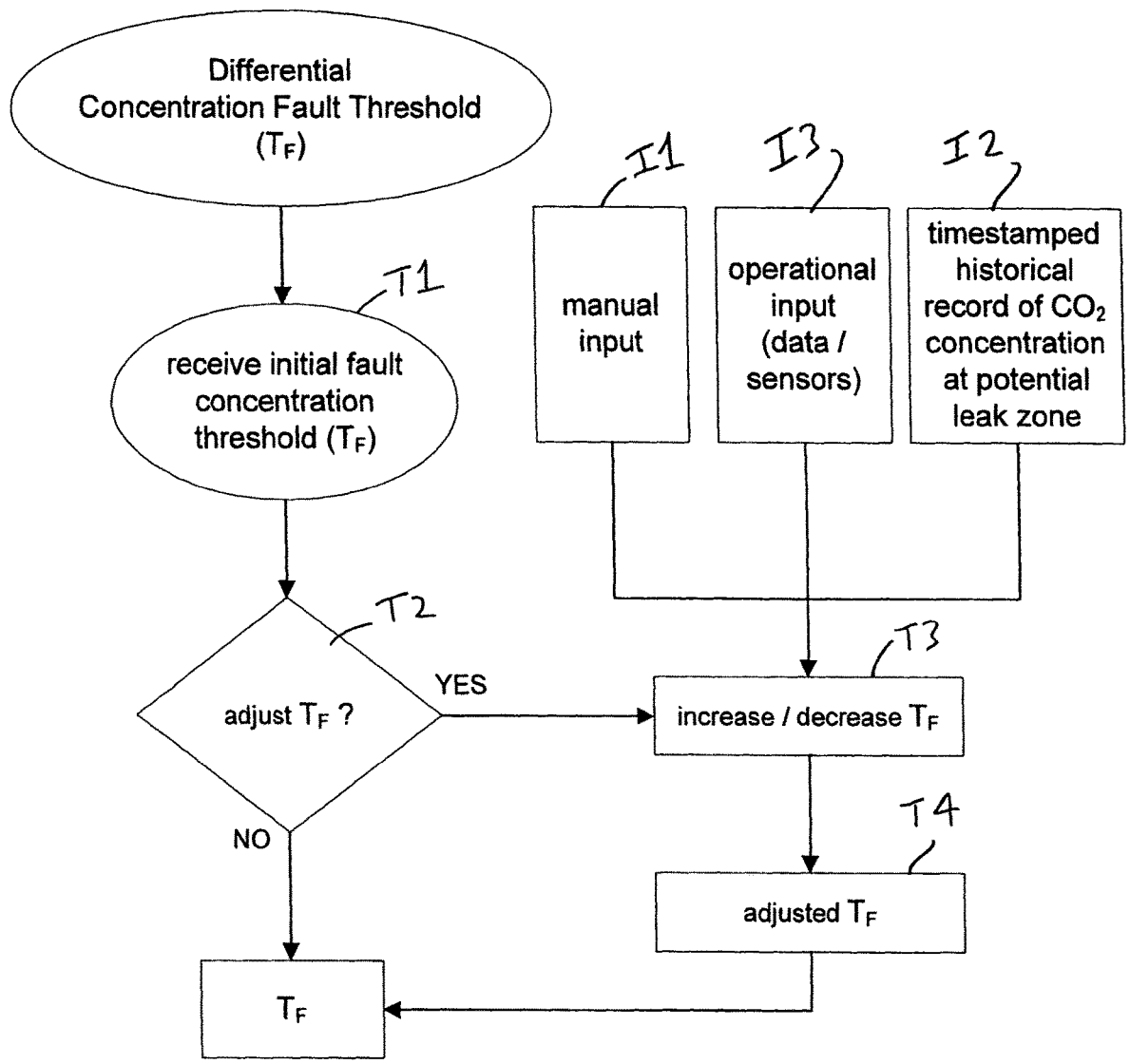
FIG. 9 is a graphical representation of one example of a logic algorithm establishing a differential concentration fault threshold value in accordance with the subject matter of the present disclosure.

The differential carbon dioxide monitoring method may include a step S1 of assigning a differential concentration fault threshold $T_F$ and assigning an alert concentration threshold $T_A$. One or both of the differential concentration fault threshold $T_F$ and the alert concentration threshold $T_A$ can be preset in the monitoring system 100 and/or one or both can be manually adjusted by a technician when the monitoring system 100 is installed or configured in the building BDG or other installation location using the input/output devices 152,156,160 or the like. The differential concentration fault threshold $T_F$ represents a carbon dioxide concentration differential magnitude between the sensed carbon dioxide concentration level $C_P$ in a potential leak zone (i.e., one of the zones ZN1-ZN6) and a reference carbon dioxide concentration level $C_{REF}$ of a reference zone that is indicative of a probable leak of carbon dioxide from a refrigeration appliance RFA in or near the potential leak zone. The alert concentration threshold $T_A$ represents an actual or absolute sensed carbon dioxide concentration level in a potential leak zone $C_P$ (i.e., one of the zones ZN1-ZN6) that is sufficiently high to require an immediate alert such as a warning message or other warning indicator provided to a warning system or to a human operator or technician. The differential concentration fault threshold $T_F$ and/or the alert concentration threshold $T_A$ may be adjusted over time such as described in more detail below with reference to FIG. 9 and/or via operator input to the monitoring system 102. Those of ordinary skill in the art will recognize that the term "threshold" as used herein can mean a value or level that must be equaled to be satisfied or a value or level that must be exceeded to be satisfied.

The differential carbon dioxide monitoring method of FIG. 7 further includes a step S2 of sensing (measuring) a potential leak zone carbon dioxide concentration $C_P$ in a monitoring zone referred to as a "potential leak zone." A potential leak zone may include one or more of the zones ZN1,ZN2 in which a carbon dioxide refrigeration appliance RFA or other source of carbon dioxide is located, and this sensing step may include measuring or sensing the carbon dioxide concentration level at an inlet 104A,104B respectively located in and associated with the potential leak zone ZN1,ZN2. The potential leak zone carbon dioxide level $C_P$ is sensed and can be stored by the monitoring unit 102.

The method can further comprise a step S3 of comparing the potential leak zone carbon dioxide concentration $C_P$ to the alert concentration threshold $T_A$ that represents an absolute carbon dioxide concentration level $C_P$ that is sufficiently high to require an immediate alert. If the monitoring unit 102 determines that the potential leak zone carbon dioxide concentration level $C_P$ satisfies the alert concentration threshold $T_A$ (i.e., the alert concentration threshold $T_A$ is met or exceeded), then the monitoring unit 102 initiates a step S6 to output a notification signal that results in output of an alert. Those of ordinary skill in the art will recognize that although FIG. 7 shows the alert concentration threshold $T_A$ as being satisfied if the potential leak zone concentration level $C_P$ is equal to or greater than the alert concentration threshold $T_A$, the alert concentration threshold $T_A$ can alternatively be satisfied if the potential leak zone concentration level $C_P$ is greater than the alert concentration threshold $T_A$. The alert can be one or more alerts including a visual alert, an audible alert, an electronic message such as a text message, e-mail, or the like, a system shutdown, and/or any other signal provided to a human technician or to a computer system using any one or more of the input output devices 152,156,160 and communication interfaces 148 of the system 100. The method can end with the alert step S6. Alternatively, as shown in broken lines, the method may further include an optional step S7 that may be carried out by a user, technician and/or a computer system to assess, repair, and reset the system 100, after which control returns to step S8 for normal operations (non-fault operations).

If the step S3 determines that the potential leak zone carbon dioxide concentration $C_P$ is less than the alert concentration threshold $T_A$, then a step S4 can be carried out in which the monitoring unit 102 derives a carbon dioxide concentration differential $C_{DF}$ that represents a differential magnitude between the sensed potential leak zone carbon dioxide concentration $C_P$ and the reference carbon dioxide concentration $C_{REF}$. As described in more detail below, the reference carbon dioxide concentration $C_{REF}$ can be input to and/or derived by the monitoring unit 102 from currently sensed carbon dioxide concentration at one or more of the monitoring inlets 104A-104F located in a reference zone ZN1-ZN6, i.e., one of the monitoring zones ZN1-ZN6 located outside the potential leak zone or the reference carbon dioxide concentration level can be input to and/or derived by the monitoring unit 102 from historical carbon dioxide concentration levels sensed in the potential leak zone, itself. In one non-limiting example, the reference concentration level $C_{REF}$ is used together with the potential leak zone concentration level $C_P$ by the monitoring unit 102 to derive the carbon dioxide concentration differential $C_{DF}$ that represents a differential between the sensed potential leak zone carbon dioxide concentration $C_P$ and the reference carbon dioxide concentration $C_{REF}$. For example, the reference concentration $C_{REF}$ can be subtracted from the potential leak zone concentration $C_P$ to derive the carbon dioxide concentration differential $C_{DF}$ that represents a carbon dioxide concentration differential between the sensed potential leak zone carbon dioxide concentration $C_P$ and the reference carbon dioxide concentration $C_{REF}$.

The method further comprises a fault assessment step S5 of determining if a carbon dioxide fault condition is present. In one example, the monitoring unit 102 compares the carbon dioxide concentration differential $C_{DF}$ with the differential concentration fault threshold $T_F$. If the carbon dioxide concentration differential $C_{DF}$ does not satisfy the differential concentration fault threshold $T_F$ (if $C_{DF}$ does not equal or exceed $T_F$ in the present example), then the method proceeds to the step S8 for normal operations of the system 100. Alternatively, if the carbon dioxide concentration differential $C_{DF}$ satisfies the differential concentration fault threshold $T_F$ (if $C_{DF}$ equals or exceeds $T_F$ in the present example), then the method proceeds to step S6 wherein the controller 116 outputs a notification signal to initiate an alert that indicates that the carbon dioxide concentration in the potential leak zone (monitoring zone) exceeds the carbon dioxide concentration in the reference zone by at least the magnitude of the concentration fault threshold $T_F$. Those of ordinary skill in the art will recognize that although FIG. 7 shows the fault threshold $T_F$ as being satisfied if the concentration level differential $C_{DF}$ is equal to or greater than the fault threshold $T_F$, the present method can alternatively be implemented such that the fault concentration threshold $T_F$ is only satisfied if the concentration level differential $C_{DF}$ is greater than the fault threshold $T_F$. The alert output in step S6 can be one or more alerts including a visual alert, an audible alert, an electronic message such as a text message, e-mail, or the like, a system shutdown, and/or any other signal provided to a human user, technician or to a computer system and such alert can be output by the system 100 via output devices 152,160 and/or via communications interface 148 or using one or more other suitable audio, visual, message, gauges, or other alert output devices. The method can end with the alert step S6. Alternatively, as shown in broken lines, the method may further include an optional step S7 that may be carried out by a user, technician and/or a computerized diagnostic system to assess, repair, and reset the system 100, after which control returns to the normal operations step S8 for normal (non-fault condition) operation of the system.

The differential carbon dioxide monitoring method of FIG. 7 optionally includes a fault persistence procedure FP. The fault persistence procedure FP comprises optionally determining the persistence of a carbon dioxide differential fault condition and only performing the alert step S6 if the carbon dioxide differential fault is determined to be persistent by the monitoring unit 102. More particularly, if the step S5 determines that a fault condition is present, the optional fault persistence procedure FP comprises a step S5a of incrementing a fault counter to record the detection of a fault condition. The fault counter can be a value, flag, or other data structure that can be stored in the memory 120 of the controller 116 or in another location of the system 100 for recording the occurrence of a faut condition. In one embodiment, the fault counter is automatically reset to zero after a select time period such as one day or a select number of hours such as 1-24 hours, for example. In another embodiment, the fault counter is not reset until such time as the assess/repair/reset step S7 is performed after an alarm event S6. A step S5b of the fault persistence procedure FP determines if the fault condition is persistent as described below. If the fault is not persistent, control passes to step S8 for normal (no fault) operations. Alternatively, if the step S5b determines that the fault is persistent, then alert step S6 is performed to provide the alert as described above, and the fault counter is cleared or reset.

The step S5b of determining if a fault is persistent is performed by the monitoring unit 102 and can use various methods for assessing the persistence of a fault. In one example, the step S5b determines a fault to be persistent if the fault counter exceeds a select absolute count or value, such as a count in the range of 2-10 recorded faults, over an undefined or open-ended time period. In another example, the step S5b determines a fault to be persistent if the fault counter exceeds a select count or value, such as a count in the range of 2-10 recorded faults, over a defined time period such as one day, one week, or a select number of minutes or hours such as 1 to 24 hours or 2-60 minutes. In another embodiment, the step S5b determines a fault to be persistent if the percentage of faults vs. non-faults exceeds a select value for a select number of cycles of the fault assessment step S5 of FIG. 7. In such case, the fault persistence determination step S5b deems a fault to be persistent if: $(x/y)*100 \geq p$ where x=the number of faults recorded by the fault counter, y=the select number of cycles of the fault assessment step S5, and p=the fault persistence percentage threshold. In one example, the number of cycles is selected as 5 (y=5) and the fault percentage threshold is set at 60% (P=60%). In such example, the step S5b finds a fault condition to be persistent as soon as the number of faults is equal to 3 (x=3) during any 5 consecutive occurrences (cycles) of the fault assessment step S5 of FIG. 7.

If the fault persistence procedure FP finds the fault to be persistent, the alert is performed at step S6 as described above and the fault counter is cleared or reset. Upon completion of the step S7 to assess/repair/reset the system, the method resumes normal operations at with step S8.

As shown in FIG. 7, the method may further comprise a step S9 of determining if the differential concentration fault threshold $T_F$ and/or the alert concentration threshold $T_A$ should be adjusted. This decision of whether or not to adjust either the differential concentration fault threshold $T_F$ or the alert concentration threshold $T_A$ can be based upon user input and/or can be based upon other factors such as a preprogrammed threshold adjustment sequence based upon actual or anticipated operating conditions for the system 100 including time data, date data, heating/ventilation/air-conditioning (HVAC) data, occupancy data, temperature data, sales data, humidity data, and other factors monitored by, derived by, and/or input to the controller 116 of the system 100 as described in more detail below with reference to FIG. 9. If the step S9 determines that neither the differential concentration fault threshold $T_F$ nor the alert concentration threshold $T_A$ should be adjusted, the method returns to step S2 of sensing a carbon dioxide concentration level in a potential leak zone $C_P$. Otherwise, if the step S9 determines that the differential concentration fault threshold $T_F$ and/or the alert concentration threshold $T_A$ should be adjusted, the method returns to step S1 where the differential concentration fault threshold $T_F$ and/or the alert concentration threshold $T_A$ is adjusted as required.

Figure 8:
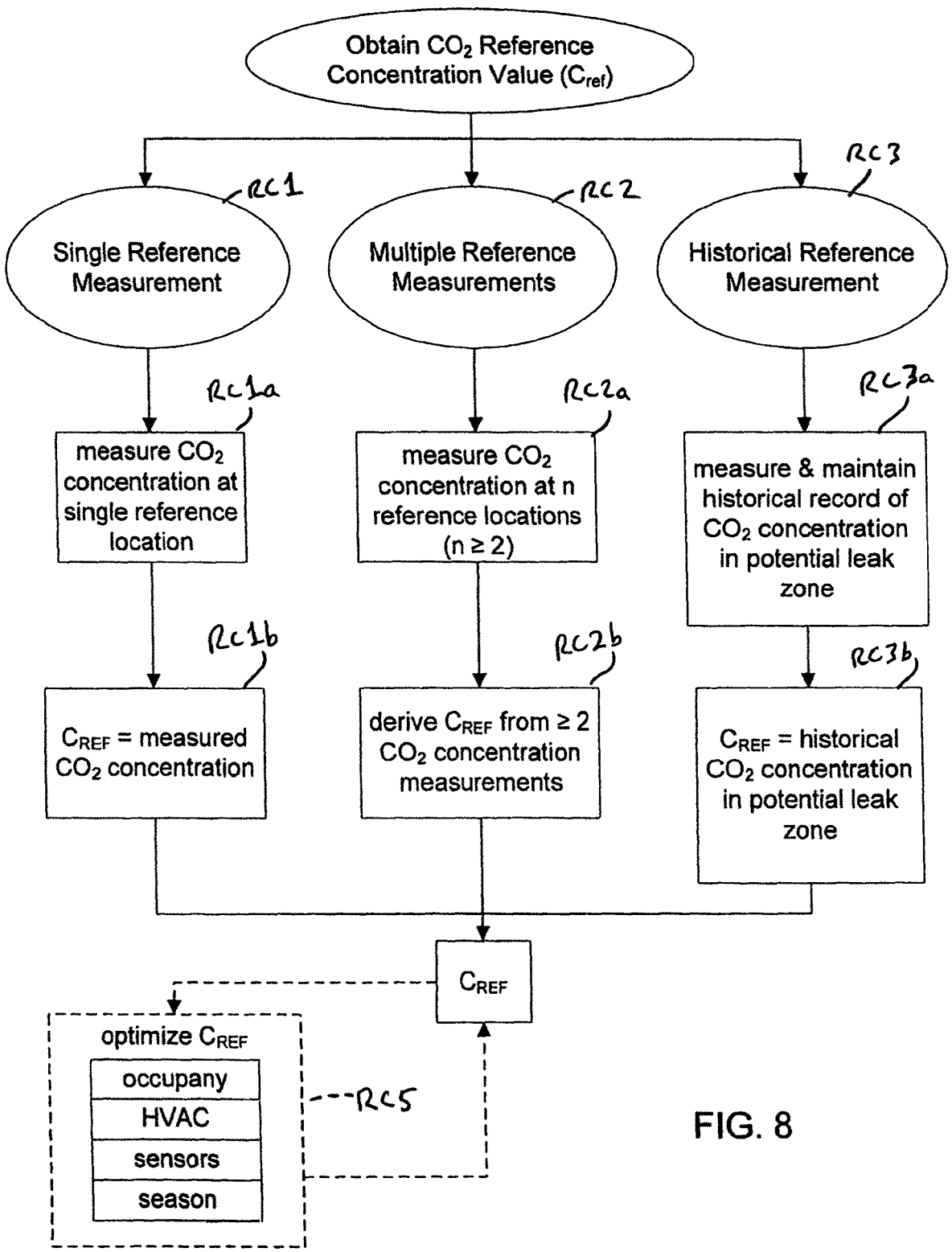
FIG. 8 is a graphical representation of one example of a logic algorithm establishing a carbon dioxide reference concentration value in accordance with the subject matter of the present disclosure.

FIG. 8 is a graphical representation of three different examples RC1,RC2,RC3 of a logic algorithm and method for establishing a carbon dioxide reference concentration value $C_{REF}$ in accordance with the subject matter of the present disclosure. In a first example method RC1, a step RC1a measures the actual carbon dioxide concentration at a single reference location by the system 100 or by a related system. In one example, the single reference location is a reference inlet provided by one of the monitoring inlets 104A-104F of the system 100 that is different from the potential leak zone inlet being used to perform the carbon dioxide sensing step S2 of FIG. 7. The reference inlet 104A-104F may be in an inlet 104A,104B located in a potential leak zone ZN1,ZN2 other than the potential leak zone inlet being monitored in the sensing step S2 of FIG. 7 or the reference inlet 104A-104F may be in a zone 104C-104F that is not a potential leak zone in that it does not include a refrigeration appliance RFA or other captured source of carbon dioxide that can leak. As such, the reference inlet 104A-104F is located in a reference zone ZN1-ZN6 that is different from the potential leak zone (monitoring zone) ZN1-ZN2 in which the carbon dioxide concentration is being sensed in step S2 of FIG. 7.

The method RC1 further includes a step RC1b that sets the carbon dioxide reference concentration value $C_{REF}$ equal to the carbon dioxide concentration sensed by the system 100 at the reference inlet 104A-104F in the reference zone ZN1-ZN6. In this embodiment, the reference inlet 104A-104F can be any one of the monitoring inlets 104A-104F except for the potential leak zone monitoring inlet located in the potential leak zone (monitoring zone) currently being monitored/tested according to the method of FIG. 7. Alternatively, the reference location can be any other location located inside or outside of the building BDG.

In a second example method RC2 of FIG. 8, the system 100 performs step RC2a to measure the actual carbon dioxide concentration at multiple reference locations or reference zones to obtain multiple carbon dioxide reference measurements respectively associated with the reference locations. In one example, the multiple reference locations are provided by multiple reference inlets selected from the plurality of monitoring inlets 104A-104F of the system 100 located in reference zones ZN1-ZN6, wherein the possible reference zones ZN1-ZN6 are the zones not including the monitoring inlet 104A-104F being used as the potential leak zone monitoring inlet by step S2 of FIG. 7. In a step RC2b the controller 116 or other processor of the system 100 derives the carbon dioxide reference concentration value $C_{REF}$ from the multiple carbon dioxide reference measurements obtained in step RC2a. In one example, the controller 116 derives the carbon dioxide reference concentration value $C_{REF}$ using a simple average of the multiple carbon dioxide reference measurements obtained in step RC2a. In another example, the controller 116 derives the carbon dioxide reference concentration value $C_{REF}$ based upon a mathematical function of the multiple carbon dioxide reference measurements such as the median, the minimum, the maximum, a weighted average based upon a physical distance of the reference location from the potential leak zone, or other function. Alternatively, the reference location(s) in which the carbon dioxide is sensed in step RC2a can be any other location located inside or outside of the building BDG.

In a third example method RC3 of FIG. 8, the system 100 performs step RC3a to measure and maintain a record of the carbon dioxide concentration in a potential leak zone ZN1, ZN2 over a select time period such as a day, week, month, and/or year. As noted, a potential leak zone is any monitoring zone ZN1-ZN6 including a refrigeration appliance RFA or other contained pressurized source of carbon dioxide that can potentially leak into the atmosphere. In a step RC3b, the controller 116 of the system 100 derives a carbon dioxide reference concentration value $C_{REF}$ based upon the one or more prior recorded carbon dioxide concentration measurements obtained in step RC3a. In this manner, the carbon dioxide reference concentration value $C_{REF}$ represents a prior carbon dioxide concentration for the same zone ZN1, ZN2 being monitored as a potential leak zone in step S2 of FIG. 7 such that a current carbon dioxide concentration in a potential leak zone ZN1,ZN2 can be compared against a prior reference carbon dioxide concentration in the same zone ZN1,ZN2.

In one example, the step RC3 optionally includes recording and storing timestamp data such as time, day and/or date data respectively representing the time, day, and/or date of the carbon dioxide concentration measurements taken in step RC3a so that the step RC3a thus maintains a timestamped historical record of the actual, average, or other prevailing carbon dioxide level in the region of each carbon dioxide monitoring inlet 104A,104B that is located in a potential leak zone ZN1,ZN2. In such case, in step RC3b, the controller 116 of the system 100 derives and assigns a carbon dioxide reference concentration value $C_{REF}$ for the potential leak zone carbon dioxide inlets 104A,104B based upon the timestamped historical record maintained in step RC3a. In this manner, the carbon dioxide reference concentration value $C_{REF}$ can be assigned in step RC3b to correspond in terms of time and/or date data to the time and/or date of the potential leak zone carbon dioxide measurement taken in step S2 of FIG. 7. The controller 116 thus correlates the current potential leak zone carbon dioxide measure taken in step S2 of FIG. 7 to a reference concentration value $C_{REF}$ in the timestamped historical record based upon corresponding time and/or date data. In this manner, the carbon dioxide reference concentration value $C_{REF}$ represents a prior actual, average, or other historical prevailing carbon dioxide concentration for the corresponding time and/or date for the same zone ZN1,ZN2 being monitored as a potential leak zone in step S2 of FIG. 7. This allows the current carbon dioxide concentration in a potential leak zone ZN1,ZN2 obtained via step S2 of FIG. 7 to be compared against a prior reference carbon dioxide concentration for the same zone ZN1,ZN2 for the same time period (time and/or date).

With continuing reference to FIG. 8, the carbon dioxide reference concentration value $C_{REF}$ can optionally be further adjusted or optimized by the controller 116 as shown at step RC5. In particular, the carbon dioxide reference concentration value $C_{REF}$ obtained via methods RC1,RC2,RC3 or otherwise obtained or input can be optimized by the controller 116 in step RC5 based upon current and/or historical factors including occupancy data for the building BDG, HVAC data for the building BDG, products sales data, and/or other sensor data obtained from sensors such as the sensors 144.

As noted above with reference to step S9 of FIG. 7, it is sometimes deemed necessary or desirable to adjust the differential concentration fault threshold $T_F$. In such case, the differential concentration fault threshold $T_F$ may be adjusted using the method as set forth in the example of FIG. 9 or another suitable adjustment method. The threshold adjustment method of FIG. 9 comprises a step T1 of receiving an initial differential concentration fault threshold $T_F$ which may be the current differential concentration fault threshold $T_F$ in use by the system 100. A step T2 determines if the differential concentration fault threshold $T_F$ is to be adjusted and, if not, the differential concentration fault threshold $T_F$ remains unchanged. If the step T2 determines that the differential concentration fault threshold $T_F$ is to be adjusted, a step T3 is performed to increase or decrease the differential concentration fault threshold $T_F$. The adjustment step T3 increases or decreases the differential concentration fault threshold $T_F$ based upon any one or more of: (i) manual input I1 by a human technician; (ii) timestamped historical carbon dioxide concentration input I2 of the ambient carbon dioxide concentration level in a potential leak zone ZN1, ZN2 and/or in a reference zone ZN3-ZN6 that is not a potential leak zone (such as from the timestamped historical record established and maintained as part of step RC3b of FIG. 8); and/or (iii) operational input I3 such as real-time sensor input from the sensors 144 and/or historical operational input. The operational input I3 can include data such as sales data, customer traffic data, HVAC data, sensor data such as temperature, humidity, time of day, door opening/closing data, and the like provided by the sensors 144 or other sensors or systems operably connected to the carbon dioxide monitoring system 100.

In one example, the differential concentration fault threshold $T_F$ associated with one or more of the potential leak zones ZN1,ZN2 can be increased during certain time periods (hours, days, weeks, and/or months) to account for a normal or expected divergence of the respective carbon dioxide concentrations in the potential leak zone ZN1,ZN2 versus the reference zone(s) ZN3-ZN6 associated with the reference concentration $C_{REF}$ to prevent false faults. This adjustment can occur where the timestamped historical record and/or real-time sensor or operational data indicates that the normal carbon dioxide concentration differential between the potential leak zone and the reference zone(s) historically increases, is predicted to increase, and/or has actually increased for a certain time period. In another example, the differential concentration fault threshold $T_F$ associated with one or more of the potential leak zones ZN1,ZN2 can be reduced during certain time periods (hours, days, weeks, and/or months) to account for a normal or expected convergence of the respective carbon dioxide concentrations in the potential leak zone ZN1,ZN2 versus the reference zone(s) ZN3-ZN6 associated with the reference concentration $C_{REF}$ to ensure that a leak (fault) is identified. This adjustment can occur where the timestamped historical record and/or real-time sensor or operational data indicates that the normal carbon dioxide concentration differential between the potential leak zone and the reference zone(s) historically decreases, is predicted to decrease, and/or has actually decreased for a certain time period.

In a step T4, the differential concentration fault threshold $T_F$ is set to equal the adjusted differential concentration fault threshold $T_F$ as adjusted in step T3. The differential concentration fault threshold $T_F$ can be a global parameter that is used for all operations of the system 100 that can be periodically adjusted as described. Alternatively, each one or a group of more than one of the monitoring inlets 104A-104F can have a dedicated differential concentration fault threshold $T_F$ that can be periodically adjusted as described. In one example, all of the potential leak zone monitoring inlets 104A,104B or a subset of one or more of the same are assigned a differential concentration fault threshold $T_F$ that can be periodically adjusted. In such case, for example, each potential leak zone monitoring inlet 104A,104B can be assigned its own dedicated differential concentration fault threshold $T_F$ that may be adjusted over time as described.

As used herein with reference to certain features, elements, components and/or structures, numerical ordinals (e.g., first, second, third, fourth, etc.) may be used to denote different singles of a plurality or otherwise identify certain features, elements, components and/or structures, and do not imply any order or sequence unless specifically defined by the claim language.

It will be recognized that numerous different features and/or components are presented in the embodiments shown and described herein, and that no one embodiment may be specifically shown and described as including all such features and components. As such, it is to be understood that the subject matter of the present disclosure is intended to encompass any and all combinations of the different features and components that are shown and described herein, and, without limitation, that any suitable arrangement of features and components, in any combination, can be used. Thus, it is to be distinctly understood claims directed to any such combination of features and/or components, whether or not specifically embodied herein, are intended to find support in the present disclosure. To aid the Patent Office and any readers of this application and any resulting patent in interpreting the claims appended hereto, Applicant does not intend any of the appended claims or any claim elements to invoke 35 U.S.C. 112(f) unless the words "means for" or "step for" are explicitly used in the particular claim.

Thus, while the subject matter of the present disclosure has been described with reference to the foregoing embodiments and considerable emphasis has been placed herein on the structures and structural interrelationships between the component parts of the embodiments disclosed, it will be appreciated that other embodiments can be made and that many changes can be made in the embodiments illustrated and described without departing from the principles hereof. Obviously, modifications and alterations will occur to others upon reading and understanding the preceding detailed description. Accordingly, it is to be distinctly understood that the foregoing descriptive matter is to be interpreted merely as illustrative of the subject matter of the present disclosure and not as a limitation. As such, it is intended that the subject matter of the present disclosure be construed as including all such modifications and alterations insofar as they come within the scope of the appended claims and any equivalents thereof.

The invention claimed is:

1. A differential monitoring system of carbon dioxide levels of an associated atmosphere within an associated building that has an associated monitoring zone within an interior space of said associated building, said differential monitoring system comprising:
   a first monitoring inlet disposed within the associated monitoring zone;
   a monitoring unit comprising a controller operable to compare a carbon dioxide level at said first monitoring inlet with a reference carbon dioxide level and determine when said carbon dioxide level at said first monitoring inlet exceeds said reference carbon dioxide level by at least a predetermined differential threshold, and
   a second monitoring inlet in spaced relation to said first monitoring unit, said second monitoring inlet being positioned within said interior space of said associated building, said controller being operable to derive said reference carbon dioxide level from carbon dioxide level measurements taken at said second monitoring inlet.

2. The differential monitoring system according to claim 1, wherein said monitoring unit is in fluid communication with a plurality of said second monitoring inlets within said interior space of said associated building, and said controller is operable to determine said reference carbon dioxide level based upon a mathematical function of carbon dioxide level measurements taken at said plurality of said second monitoring inlet.

3. The differential monitoring system according to claim 2 wherein said carbon dioxide levels taken at said plurality of second monitoring inlets are taken contemporaneously with said carbon dioxide level at said first monitoring inlet.

4. The differential monitoring system according to claim 1, wherein said second monitoring inlet is located in the associated monitoring zone or in an associated reference zone within said interior space of said associated building that is different from the associated monitoring zone.

5. The differential monitoring system according to claim 1, wherein said monitoring unit is in fluid communication with one or more of said first and second monitoring inlets, and said controller is operable to determine said carbon dioxide levels at said one of more of said first and second monitoring inlets.

6. The differential monitoring system according to claim 1, further comprising a first sensor communicatively coupled with said controller and including said first monitoring inlet, said first sensor operable to determine a carbon dioxide level of the associated atmosphere around said first monitoring inlet.

7. The differential monitoring system according to claim 1, further comprising:

a first sensor communicatively coupled with said controller and including said first monitoring inlet, said first sensor operable to determine a carbon dioxide level at said first monitoring inlet;

a second sensor communicatively coupled with said controller and including said second monitoring inlet, said second sensor operable to determine a carbon dioxide level at said second monitoring inlet.

8. The differential monitoring system according to claim 1, wherein said controller is operable to derive said reference carbon dioxide level from carbon dioxide level measurements taken at said second monitoring inlet over a historical period of time.

9. The differential monitoring system according to claim 1, wherein said controller is operable to generate an alert representing that a potential carbon dioxide leak condition has occurred if said carbon dioxide level at said first monitoring inlet exceeds said reference carbon dioxide level by at least a predetermined differential threshold or if said carbon dioxide level at said first monitoring inlet exceeds an absolute alert threshold.

10. The differential monitoring system according to claim 1, further comprising a third monitoring inlet disposed within an associated atmospheric reference zone within the interior space of the associated building that is spaced away from the associated monitoring zone, wherein said controller is operable to: (i) compare said carbon dioxide level at said first monitoring inlet with carbon dioxide levels at said second and third monitoring inlets;

and (ii) determine when said carbon dioxide level at said first monitoring inlet exceeds carbon dioxide level at at least one of said second and third monitoring inlets by said predetermined differential threshold.

11. The differential monitoring system according to claim 10, wherein said controller derives said reference carbon dioxide level from said carbon dioxide levels measured at said second and third monitoring inlets.

12. The differential monitoring system according to claim 11, wherein said controller is operable to derive said reference carbon dioxide level from carbon dioxide levels measured at said second and third monitoring inlets over a historical period of time.

13. A differential monitoring system of carbon dioxide levels of an associated atmosphere within an associated building that has an associated monitoring zone, said differential monitoring system comprising:

a first monitoring inlet disposed within the associated monitoring zone, a monitoring unit comprising a controller operable to compare a carbon dioxide level at said first monitoring inlet with a reference carbon dioxide level and determine when said carbon dioxide level at said first monitoring inlet exceeds said reference carbon dioxide level by at least a predetermined differential threshold, wherein said predetermined differential threshold is variable, and said controller is operable to establish said predetermined differential threshold for a given period of time.

14. The differential monitoring system according to claim 13, wherein said controller is operable to establish said predetermined differential threshold based on historical carbon dioxide concentration levels in at least one of said monitoring zone and a reference zone located outside said monitoring zone.

15. A differential monitoring system of carbon dioxide levels of an associated atmosphere within an associated building that has an associated monitoring zone, said differential monitoring system comprising:

a first monitoring inlet disposed within the associated monitoring zone;

a monitoring unit comprising a controller operable to compare a carbon dioxide level at said first monitoring inlet with a reference carbon dioxide level and determine when said carbon dioxide level at said first monitoring inlet exceeds said reference carbon dioxide level by at least a predetermined differential threshold wherein said controller is further operable to determine, at measurement cycles, if said carbon dioxide level at said first monitoring inlet exceeds said reference carbon dioxide level by a predetermined differential threshold for at least three out of five successive measurement cycles, wherein said controller generates an alert representing that a potential carbon dioxide leak condition has occurred if said carbon dioxide level at said first monitoring inlet exceeds said reference carbon dioxide level by a predetermined differential threshold for at least three out of five successive measurement cycles.

16. A differential monitoring method for monitoring carbon dioxide levels within an associated building comprising a monitoring zone within an interior space of said associated building and including an associated quantity of captured carbon dioxide, said differential monitoring method comprising:

determining a first carbon dioxide concentration level, the first carbon dioxide concentration level being of a first position within the monitoring zone;

determining a reference carbon dioxide concentration level at a second position within said interior space of said building, different from the first position; and, determining if the first carbon dioxide concentration level exceeds the reference carbon dioxide concentration level by at least a differential threshold.

17. The method according to claim 16, further comprising initiating an alert if the first carbon dioxide concentration level exceeds the reference carbon dioxide concentration level by at least the differential threshold or if said carbon dioxide concentration level exceeds an absolute alert threshold.

18. The method according to claim 17, further comprising determining said reference carbon dioxide concentration level from a mathematical function of carbon level dioxide level measurements at a plurality of said second positions within said interior space of said associated building.

19. The method according to claim 18, wherein the reference carbon dioxide concentration level is of the first position which is in a reference zone within said interior space of said associated building and spaced from the monitoring zone.

20. The method according to claim 18, wherein the reference carbon dioxide concentration level is derived from a plurality of carbon dioxide concentration measurements respectively taken in a plurality of different reference zones within said interior space of said associated building that are each spaced from the monitoring zone.

* * * * *